(12) United States Patent
Filho et al.

(10) Patent No.: US 8,318,465 B2
(45) Date of Patent: Nov. 27, 2012

(54) PROCESS FOR INTERGRATED UTILIZATION OF THE ENERGY AND MATERIAL CONTENTS OF HYDROLYSATES

(75) Inventors: Murillo Villela Filho, Bottrop-Kirchhellen (DE); Isabelle Schaarschmidt, Steinheim (DE); Bernd Wahl, Karlsruhe (DE); Elmar Rother, Darmstadt (DE); Hartmut Zimmermann, Biberach (DE); Andreas Karau, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 1025 days.

(21) Appl. No.: 12/101,759

(22) Filed: Apr. 11, 2008
(Under 37 CFR 1.47)

(65) Prior Publication Data
US 2009/0098598 A1    Apr. 16, 2009

(30) Foreign Application Priority Data

Apr. 12, 2007    (DE) .......................... 10 2007 017 184

(51) Int. Cl.
| | |
|---|---|
| C12P 5/02 | (2006.01) |
| C12P 1/00 | (2006.01) |
| C12P 13/24 | (2006.01) |
| C12P 13/22 | (2006.01) |
| C12P 13/20 | (2006.01) |
| C12P 13/14 | (2006.01) |
| C12P 13/12 | (2006.01) |
| C12P 13/10 | (2006.01) |
| C12P 13/08 | (2006.01) |
| C12P 13/06 | (2006.01) |
| C12P 39/00 | (2006.01) |

(52) U.S. Cl. ........... 435/167; 435/41; 435/42; 435/71.1; 435/106; 435/107; 435/108; 435/109; 435/110; 435/113; 435/114; 435/115; 435/116

(58) Field of Classification Search .................... 435/41, 435/42, 71.1, 106, 107, 108, 109, 110, 113, 435/114, 115, 116, 167
See application file for complete search history.

(56) References Cited

U.S. PATENT DOCUMENTS

| | | | |
|---|---|---|---|
| 3,708,395 A * | 1/1973 | Nakayama et al. ........... 435/115 |
| 6,555,350 B2 * | 4/2003 | Ahring et al. ................. 435/162 |
| 2005/0153410 A1 | 7/2005 | Hallberg |
| 2007/0122874 A1 * | 5/2007 | Suthanthararajan et al. ... 435/41 |
| 2007/0190626 A1 | 8/2007 | Wilkening |
| 2007/0298477 A1 * | 12/2007 | Kratochvil et al. ........... 435/165 |
| 2009/0162892 A1 | 6/2009 | Pompojus |

FOREIGN PATENT DOCUMENTS

| | | |
|---|---|---|
| DE | 103 27 954 | 1/2005 |
| EP | 08 10 2622 | 8/2011 |
| JP | 57152890 | 9/1982 |
| WO | 2004/113549 | 12/2004 |
| WO | 2005/116228 | 12/2005 |

* cited by examiner

*Primary Examiner* — Herbert J Lilling
(74) *Attorney, Agent, or Firm* — Pillsbury Winthrop Shaw Pittman LLP

(57) ABSTRACT

A process for integrated utilization of the energy and material contents of hydrolysates and solids obtained in the enzymatic hydrolysis of renewable raw materials, in which the resulting hydrolysis solution is used as a carbon source in fermentations and the unhydrolysed solids are sent to biogas production.

14 Claims, 7 Drawing Sheets

PROCESS FOR INTERGRATED UTILIZATION OF THE ENERGY AND MATERIAL CONTENTS OF HYDROLYSATES

CROSS-REFERENCE TO RELATED APPLICATIONS

Priority is claimed to German Patent Application No. 102007017184.8 filed 12 Apr. 2007, the entirety of which is incorporated herein.

BACKGROUND OF THE INVENTION

1. Field of the Invention

The invention relates to a process for integrated utilization of the energy and material contents of hydrolysates and solids obtained in the enzymatic hydrolysis of renewable raw materials, in which the resulting hydrolysis solution is used as a carbon source in fermentations and the unhydrolysed solids are sent to biogas production.

2. Background of the Invention

Fermentative processes for preparing target substances, for example amino acids, vitamins and carotenoids, by means of microorganisms are common knowledge. Depending on the different process conditions, different carbon sources are utilized. These range from pure sucrose through raw molasses from beet and sugar, so-called "high-test molasses" (inverted sugar molasses), up to and including glucose from starch hydrolysates. For the biotechnology production of L-lysine, acetic acid and ethanol are additionally mentioned as cosubstrates usable on the industrial scale (Pfefferle et al., Biotechnogical Manufacture of Lysine, Advances in Biochemical Engineering/Biotechnology, Vol. 79 (2003), 59-112).

An important carbon source for the fermentation of microorganisms is starch. This first has to be liquefied and saccharified in preceding reaction steps before it can be utilized as a carbon source in a fermentation. To this end, the starch is obtained from a natural starch source such as potatoes, cassava, cereal, e.g. wheat, maize, barley, rye or rice, typically in prepurified form, then enzymatically liquefied and saccharified in order then to be used in the actual fermentation to produce the target substances.

More recent techniques are concerned with improved methods which are intended to enable the production of fermentation media from renewable resources (EP 1205557, US 2002/079268).

A fermentative process has also already been described, with which it is said to be possible to use starch as a carbon source (WO 2005116228).

A fermentation does not only form the desired product, but always biomass too. This biomass is either disposed of as a waste product or has to be utilized in another way and reduces the yield (product per reactant) of the process by virtue of its formation. In fermentative ethanol preparation, complex animal feeds are therefore often produced as coproducts. In the so-called dry-milling process, by which about 65% of the ethanol is prepared, nearly four tons of DDGS (distillers dried grains with solubles) are produced in the United States of America alone (Lyons 2003, Jacques 2003). In summary, the so-called dry-milling process can be described as follows: the cereal grains are ground to fine particles in a mill and mixed with liquid. This slurry is then treated with a liquefying enzyme in order to hydrolyse the cereal to dextrins, which are a mixture of oligosaccharides. The hydrolysis of starch with the liquefying enzyme, known as α-amylase, is carried out above the gelation temperature of the cereal. The slurry is boiled at an appropriate temperature to break up the granular structure of the starch and to trigger the gelation. Finally, the dextrins formed are hydrolysed further to glucose with the exoenzyme glucoamylase in a saccharization process. The DDGS obtained is the main coproduct in ethanol production. Approximately 80% of this DDGS is fed to ruminants. This means that the utilization is only economically viable if enough ruminant breeding operations are present in the vicinity of the production plant as recipients for the DDGS.

This utilization of by-products of fermentative ethanol preparation as complex animal feed must, however, be distinguished from the preparation of target substances suitable as animal feed additives. In these processes, for example, amino acids or vitamins are produced by fermentation as main products and find use in animal nutrition. In the fermentation process, complex by-products are additionally obtained, which comprise the biomass. One means of utilizing the by-products is the production of fertilizers from the fermentation broth (Ideka 2003). For lysine preparation, processes in which the product is not purified after the fermentation but rather the biomass is also sold as a constituent of the animal feed additive are also used (Biolys® U.S. Pat. No. 5,431,933). As a further idea for utilization of the biomass obtained, biomass recycling has been published (Blaesen et al. 2005). In this process, the average yield can be increased and the amount of waste to be disposed off can be reduced in fermentation processes by recycling the biomass obtained as reactants into the fermentation.

The prior art discloses the anaerobic degradation of organic substances by bacteria to form biogas which consists of methane to an extent of 50-85%. The energy stored in biogas and obtained is referred to as renewable in that it stems from renewable organic substance. In addition, the energetic utilization of biogas, in contradistinction to the combustion of natural gas, mineral oil or coal, is carbon dioxide-neutral because the carbon dioxide which forms moves within the natural carbon cycle and is consumed again by the plants during their growth.

Biogas is a high-value energy source, i.e. it can be utilized in many ways and with high efficiency. The main intake source in biogas production is currently the yield from power generation. By means of the so-called power-heat coupling, the biogas is used in a classical manner as a fuel in an internal combustion engine which drives a generator for generating mains current (alternating current). The waste engine heat from cooling system and exhaust gas which is obtained simultaneously can be utilized for heating. As an alternative to power generation with high efficiency, fuel cells are also already being used. Biogas can also be produced from wastes of L-lysine production (Viesturs et al. 1987 Proc. Latv. Acad. Sci 8 (841):102-105). A further process is said, in an integrated process, to enable the parallel production of meat (or milk), ethanol, animal feed and biogas (biofertilizer) (US 2005/0153410). In the case of use of protein-containing coreactants in anaerobic fermentation processes, difficulties can be encountered, since the proteins, in the event of changes in the pH in the presence of divalent cations, can undergo structural changes which can prevent a later enzymatic attack (Mulder 2003, Biological wastewater treatment for industrial effluents; technology and operation, Paques B. V., Balk 3.1 Fermentation).

The typical degradation process of organic material to biogas consists essentially of four stages.

In the first stage (hydrolysis), aerobic bacteria convert the high molecular weight organic substances (protein, carbohydrates, fat, cellulose) with the aid of enzymes to low molecular weight compounds such as simple sugars, amino acids, fatty acids and water. The enzymes excreted by the hydrolytic bacteria adhere to the outside of the bacteria (so-called exoenzymes) and split the organic constituents of the substrate hydrolytically into small water-soluble molecules. In the second stage (acidification), the individual molecules are degraded and converted intracellularly by acid-forming bacteria. These are possibly aerobic species which consume the oxygen still remaining and thus provide the anaerobic conditions needed for the methane bacteria. Here, mainly short-chain fatty acids, low molecular weight alcohols and gases are obtained. In the third stage (acetic acid formation), acetic acid bacteria produce the starting materials for the methane formation (acetic acid, carbon dioxide and hydrogen) from the organic acid. In the fourth stage (methane formation), methane bacteria form the methane (Eder and Schulz 2006).

The costs for the provision of the carbon source, just like the energy costs, have a considerable influence on the margins in the fine chemicals business. The most significant item in the preparation costs of, for example, L-lysine is the carbon source (Pfefferle et al. 2003). The price of sugar is subject to high variations and has a major influence on the economic viability of the fermentation processes, especially in the case of the low-cost mass products such as monosodium glutamate, L-lysine-HCl and L-threonine, whose market is determined greatly by the competition (Ikeda 2003). The provision of carbon sources suitable for fermentative utilization from favourable renewable raw materials is, however, not trivial in industry. In the workup of these carbon sources by hydrolysis, fibrous plant residues are obtained as waste products to be disposed of. In addition, biomass forms in the fermentation as a waste product to be disposed of. When biogas production is selected as a disposal process, difficulties can be encountered in the use of protein-containing coreactants in the anaerobic fermentation process used. In the event of changes in the pH in the presence of divalent cations, the proteins can undergo structural changes which can prevent later enzymatic attack (Mulder 2003). Variations in quality of the raw materials additionally hinder a stable and reproducible process regime in the biogas production.

BRIEF SUMMARY OF THE INVENTION

It is an object of the present invention to provide an integrated process for preparing target substances from renewable raw materials, in which a lower level of waste substances occurs and the energy content of the raw materials is utilized better.

The invention provides a process for integrated utilization of the energy and material contents of solutions and solids obtained in the enzymatic hydrolysis of renewable raw materials, comprising:
a) the preparation of an aqueous hydrolysis mixture comprising at least one carbon source utilizable by the microorganism used to prepare a target substance from renewable raw materials by enzymatic hydrolysis,
b) the use of this aqueous mixture in the preparation of a target substance preferably having at least 3 carbon atoms or at least 2 carbon atoms and at least 1 nitrogen atom by fermentation, wherein
c) before step b), the solid constituents from the hydrolysis mixture obtained in step a) are removed, and
d) these solid constituents, which are especially of fibrous nature, are subjected to an anaerobic cofermentation for the production of biogas.

DETAILED DESCRIPTION OF THE INVENTION

Figure 1:
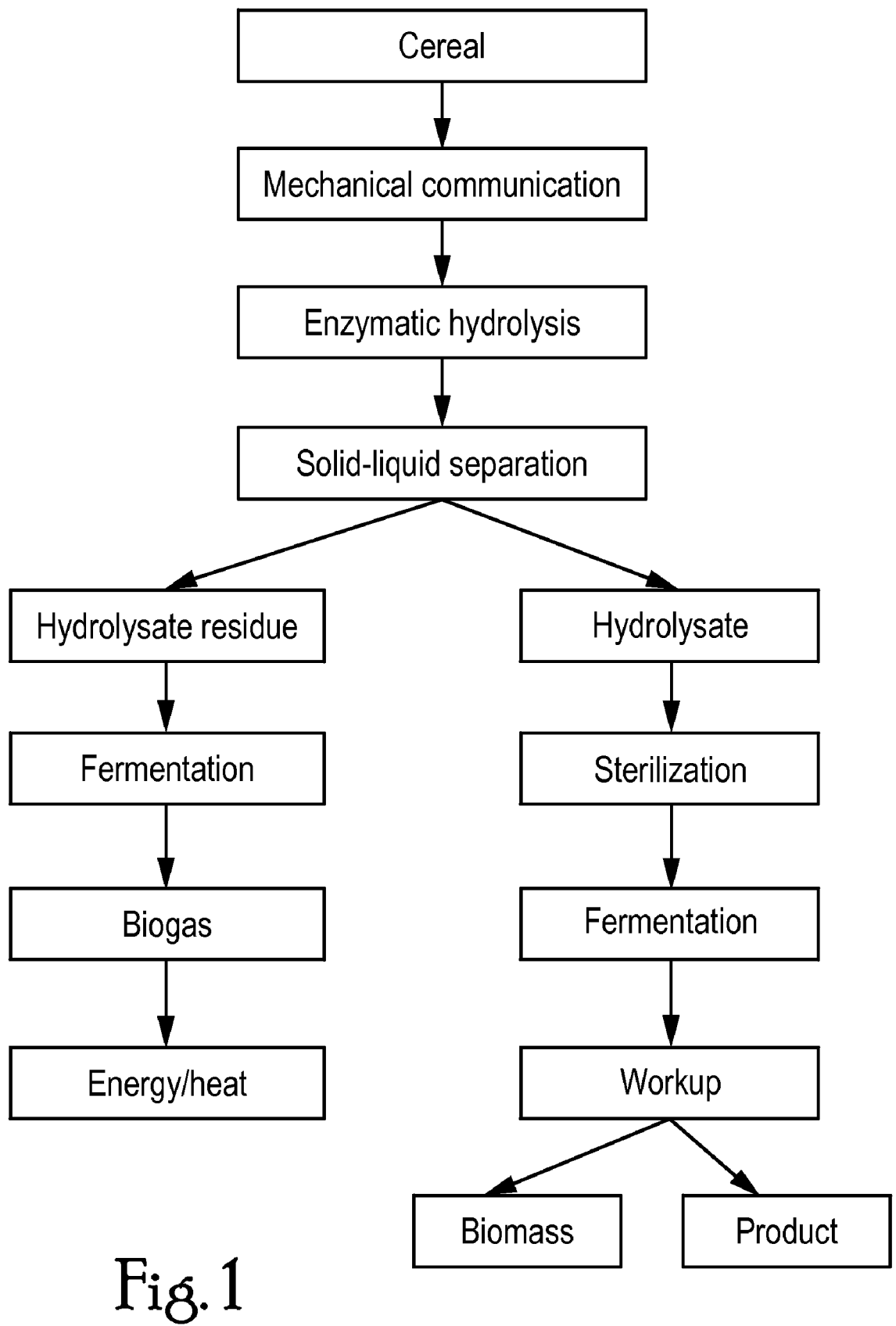
FIG. 1 is a flow-chart depicting an embodiment of the invention demonstrating the overall process of producing target substances by fermentation of renewable raw materials (e.g., cereals).

Biogas can be converted to thermal energy or electrical energy by combustion. At the same time, heat is also formed in step d) (see FIG. 1).

Useful starch sources include in particular dry grains or seeds which, in the dried state, have a starch content of at least 40% by weight and preferably at least 50% by weight. These can be found in many of the cereal plants cultivated on a large scale, such as maize, wheat, oats, barley, rye, rice and various millet types, for example sorghum and milo. A preferred starch source is cereal, more preferably selected from maize, barley and wheat. In principle, the process according to the invention can also be performed with other starch sources, for example potatoes, tapioca or a mixture of different starch-containing fruits or seeds.

The mixtures prepared by enzymatic hydrolysis comprise sugars, which are preferably monosaccharides such as hexoses and pentoses, e.g. glucose, fructose, mannose, galactose, sorbose, xylose, arabinose and ribose, especially glucose. The proportion of monosaccharides other than glucose may vary depending on the starch source used and the non-starch-containing constituents present therein.

These hydrolysis processes are known from the prior art (WO 2005/116228).

The sugar-containing nutrient medium prepared from the hydrolysis mixture after removal of the remaining solids is used for fermentative preparation of target substances having at least 3 carbon atoms or at least 2 carbon atoms and at least 1 nitrogen atom. To this end, the mixture prepared in step a), after removal of the solids, is sent to a fermentation according to b). The fermentation process can be performed in a typical manner known to those skilled in the art.

The term "target substance" hereinafter includes organic mono-, di- and tricarboxylic acids which optionally bear 1 or more, e.g. 1, 2, 3 or 4, hydroxyl groups and have preferably 3 to 10 carbon atoms, for example tartaric acid, itaconic acid, succinic acid, fumaric acid, maleic acid, 2,5-furandicarboxylic acid, 3-hydroxypropionic acid, glutaric acid, laevulinic acid, lactic acid, propionic acid, gluconic acid, aconitic acid and diaminopimelic acid, citric acid; especially proteinogenic amino acids and non-proteinogenic amino acids, preferably lysine, methionine, phenylalanine, tryptophan and threonine; purine and pyrimidine bases; nucleosides and nucleotides, e.g. nicotinamide adenine dinucleotide (NAD) and adenosine 5'-monophosphate (AMP); lipids; saturated and unsaturated fatty acids having preferably 10 to 22 carbon atoms, e.g. γ-linolenic acid, dihomo-γ-linolenic acid, arachidonic acid, eicosapentaenoic acid and docosahexaenoic acid; diols having preferably 3 to 8 carbon atoms, e.g. propanediol and butanediol; polyhydric alcohols having 3 or more, e.g. 3, 4, 5 or 6, OH groups, e.g. glycerol, sorbitol, mannitol, xylitol and arabitol; relatively long-chain alcohols having at least 4 carbon atoms, e.g. having 4 to 22 carbon atoms, e.g. butanol; carbohydrates, e.g. hyaluronic acid and trehalose; aromatic compounds, e.g. aromatic amines, vanillin and indigo; vitamins and provitamins, e.g. ascorbic acid, vitamin $B_6$, vitamin $B_{12}$ and riboflavin; proteins, e.g. enzymes, carotenoids, e.g. lycopene, β-carotene, astaxanthin, zeaxanthin and canthaxanthin; ketones having preferably 3 to 10 carbon atoms and optionally 1 or more hydroxyl groups, e.g. acetone and acetoin; lactones, e.g. γ-butyrolactone, cyclodextrins, biopolymers, e.g. polyhydroxyacetate, polyesters, polysaccharides, polyisoprenoids, polyamides, polyhydroxyalkanoates, e.g. poly-3-hydroxybutyric acid and copolyesters with other organic hydroxycarboxylic acids such as 3-hydroxyvaleric acid, 4-hydroxybutyric acid and others, which are described in Steinbüchel (Ed.), Biopolymers, 1st edition, 2003, Wiley-VCH, Weinheim and the literature cited there; and precursors and derivatives of the aforementioned compounds. Further compounds useful as target substances are described by Gutcho in Chemicals by Fermentation, Noyes Data Corporation (1973), ISBN: 0818805086.

Microorganisms used in accordance with the invention are preferably selected from the genera *Corynebacterium, Bacillus, Ashbya, Escherichia, Aspergillus, Alcaligenes, Actinobacillus, Anaerobiospirillum, Lactobacillus, Propionibacterium* and *Clostridium*, especially from strains of *Corynebacterium glutamicum, Bacillus subtilis, Ashbya gossypii, Escherichia coli, Aspergillus niger* or *Alcaligenes latus, Anaerobiospirillum succiniproducens, Actinobacillus succinogenes, Lactobacillus delbrueckii, Lactobacillus leichmanni, Propionibacterium arabinosum, Propionibacterium schermanii, Propionibacterium freudenreichii, Clostridium propionicum* and *Clostridium acetobutlicum*.

In a preferred embodiment, the target substance prepared by fermentation is L-lysine. To perform the fermentation, it is possible here to employ analogous conditions and procedures as described, for example, in Pfefferle et al., loc. cit. and in U.S. Pat. No. 3,708,395. In principle, either a continuous or a batchwise (batch or fed-batch) operating mode is useful; preference is given to the fed-batch operating mode.

The performability of the process according to the invention is shown with reference to the enzymatic hydrolysis of whole-corn flour, fine whole-wheat meal, whole-rye flour (type 1159) and fine whole-rye meal with three different enzymes. The solid phase (fibre fraction) is removed by filtration under pressure, filtration in a centrifugal field, sedimentation in a centrifugal field and washing out. The nutrient medium obtained from the hydrolysate is concentrated in a vacuum rotary evaporator and then sterilized by autoclaving. The suitability of such a processed wheat hydrolysate as a carbon source for the fermentative preparation of fine chemicals has been demonstrated by the example of L-lysine preparation with the strain *Brevibacterium flavum* DM1730 (Georgi et al. 2005), both in shaken-flask experiments with a batchwise process and in a stirred tank in a feed process. Surprisingly, it was found that the experiments with hydrolysate led to significantly improved space-time yields compared to the control experiment with standard glucose solution.

The hydrolysate residue or fermentation residue removed is fermented by processes known from the prior art.

A biogas reactor can be charged continuously or batchwise. In the case of batchwise charging, the so-called batch principle, the whole digestion vessel is filled all at once. The charge is digested without a change in substrate up to the end of the residence time selected. The gas production sets in after the filling, reaches a maximum and then levels off. After the residence time has elapsed, the vessel is emptied completely apart from a residue which acts as a seed material for the next charge.

For rapid filling and emptying, as well as the digestion vessel, a reservoir and storage tank of the same size is needed. Inhomogeneous gas production can be balanced out by a plurality of relatively small fermenters which are filled in a phase-off set manner. However, several relatively small tanks cause higher specific costs. Another disadvantage is the degradation processes associated with methane losses in the preliminary tank during the long period before the digestion vessel is emptied.

For these reasons, the demand for the batchwise process technology is very low. However, it is selected for laboratory experiments in order to investigate a substrate for its behaviour in the fermenter and its gas yields.

Advantageous fermenters are those which are charged continuously with the substances to be fermented, while a corresponding amount of fully digested substrate is simultaneously pumped out. As a result, permanent digestion with constant gas production is achieved and, moreover, acidification is prevented by the frequent addition of small amounts of substrates.

The biogas plant for the preferably combined fermentation of the hydrolysate residue and that of the fermentation residue is therefore designed especially as a continuously charged plant.

The anaerobic degradation is conducted by a mixed population of bacteria in various temperature ranges, a distinction being drawn between thermophilic and mesophilic methods. Bacteria of this type are present in the customary sewage sludge from treatment plants.

The mesophilic method is found to be more stable than the thermophilic method in the event of temperature variations.

Good mixing and distribution influence the rate and completeness of anaerobic degradation to a high degree. Vigorous mixing reduces temperature and pH gradients within the fermenter and enables easy exit of the gas bubbles. At the same time, formation of floating and sinking layers is reduced or prevented and good mixing of the fresh substrate with the digested substrate is achieved. Excessive mixing is opposed by the high energy input. Moreover, gentle circulation is desirable for good methanization in order not to adversely affect the symbiosis between the acetogenic and methanogenic microorganism groups by shear stress, since the methane production otherwise falls.

The residence time of the substrate is an important parameter for choosing the dimensions of the biogas reactor. Even though the theoretically necessary residence time for degradation of the organics in laboratory batch experiments is much shorter, 50-80 days have been found to be useful in practice for the digestion of renewable raw materials and agricultural fertilizers. An important parameter which incorporates the residence time is the so-called digestion space velocity. This refers to the amount of organic dry substance which is fed daily to the fermenter. It is reported in kilograms of organic dry substance per m³ of fermenter volume and day. Optimization of the digestion space velocity is one of the most important points for efficient operation of a biogas plant. Excessively low space velocity is unfavourable, since the given capacities are not exploited fully and a biogas plant thus does not yield the maximum economic profit. An excessive space velocity leads to instability of the fermentation process, which endangers continuous operation of the plant.

Biogas formation from the wheat hydrolysate residue (fibre content), from the fermentation residue (excess biomass) and from a mixture of the two (by so-called cofermentation) has been tested experimentally. In detail, the biogas potential, i.e. composition of the biogas and the amount of the constituents, is determined with a suitable test setup. The results from the digestions of the wheat hydrolysate and of the fermentation residue, and also from the cofermentation, were compared. It was found that higher specific biogas yields can be achieved in the cofermentation than in the case of separate fermentation of fibre residues of biomass waste alone. Surprisingly, the high protein content of the biomass had no adverse effect on the biogas production.

Figure 2:
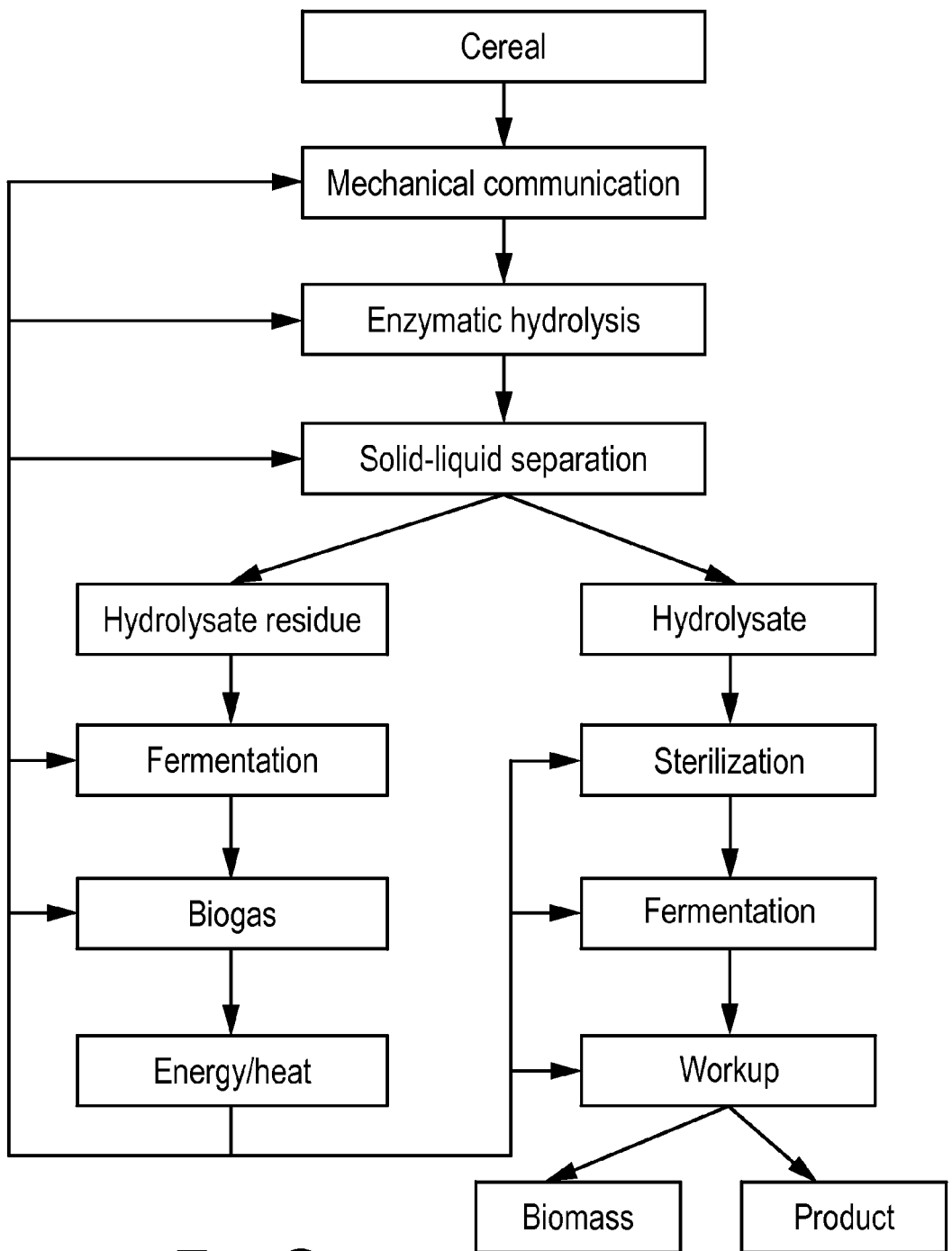
FIG. 2 is a flow-chart depicting an embodiment of the invention demonstrating how energy and/or heat produced from the combustion of biogas may be introduced at one or more steps of the overall process.
Figure 3:
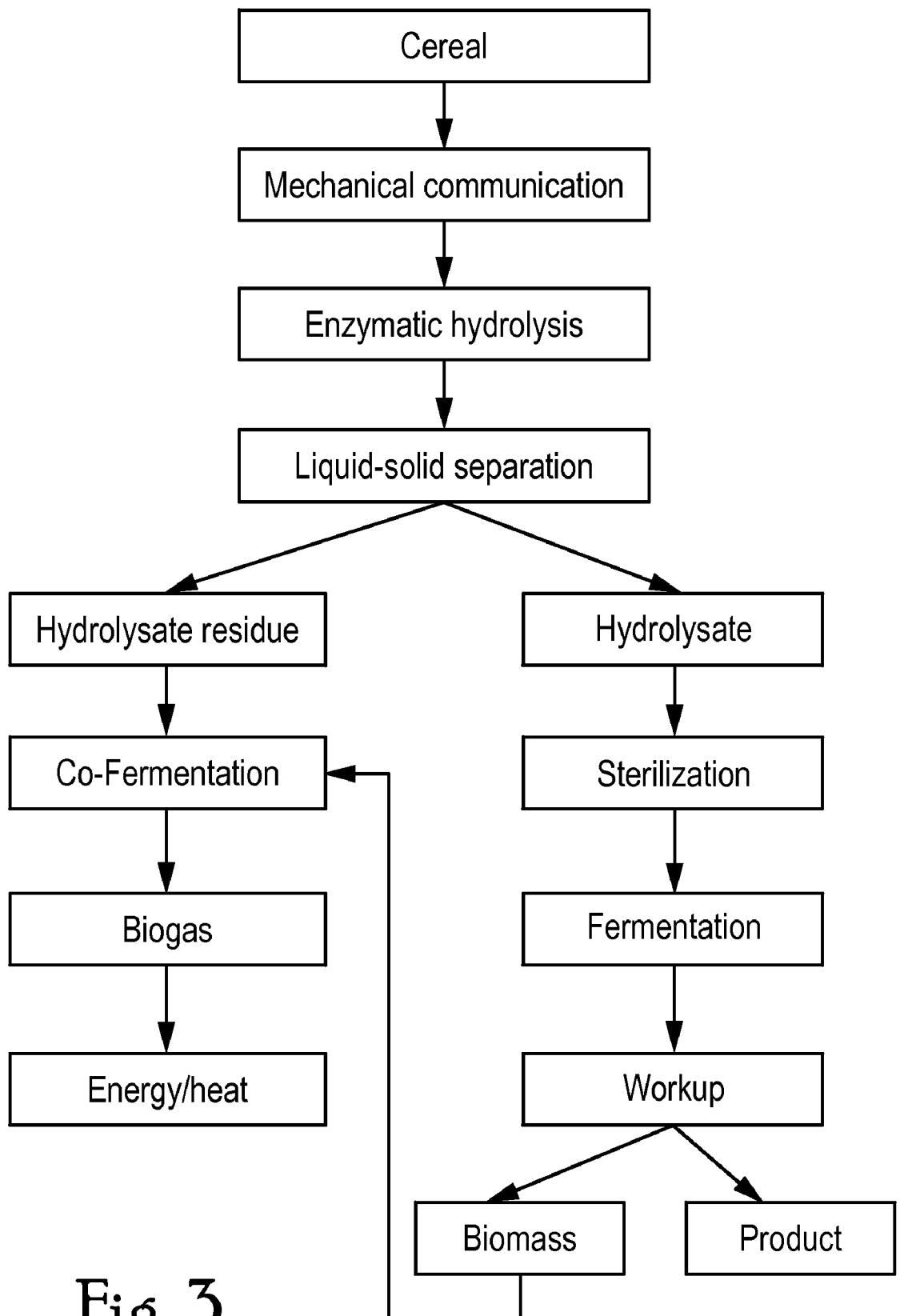
FIG. 3 is a flow-chart depicting an embodiment of the invention demonstrating how biomass waste produced from the fermentation of the hydrolysate may be fed into the anaerobic fermentation step to produce additional biogas through co-fermentation.

The invention likewise provides a process in which the energy/heat obtained in step d) from the process is introduced into the integrated process according to the invention at one or more suitable points (see FIG. 2). It is also possible to feed the biomass obtained in the aerobic fermentation to prepare the target substances into the anaerobic fermentation to prepare the biogas, whose utilizable constituent consists of methane, and to allow it to ferment there (see FIG. 3).

Figure 4:
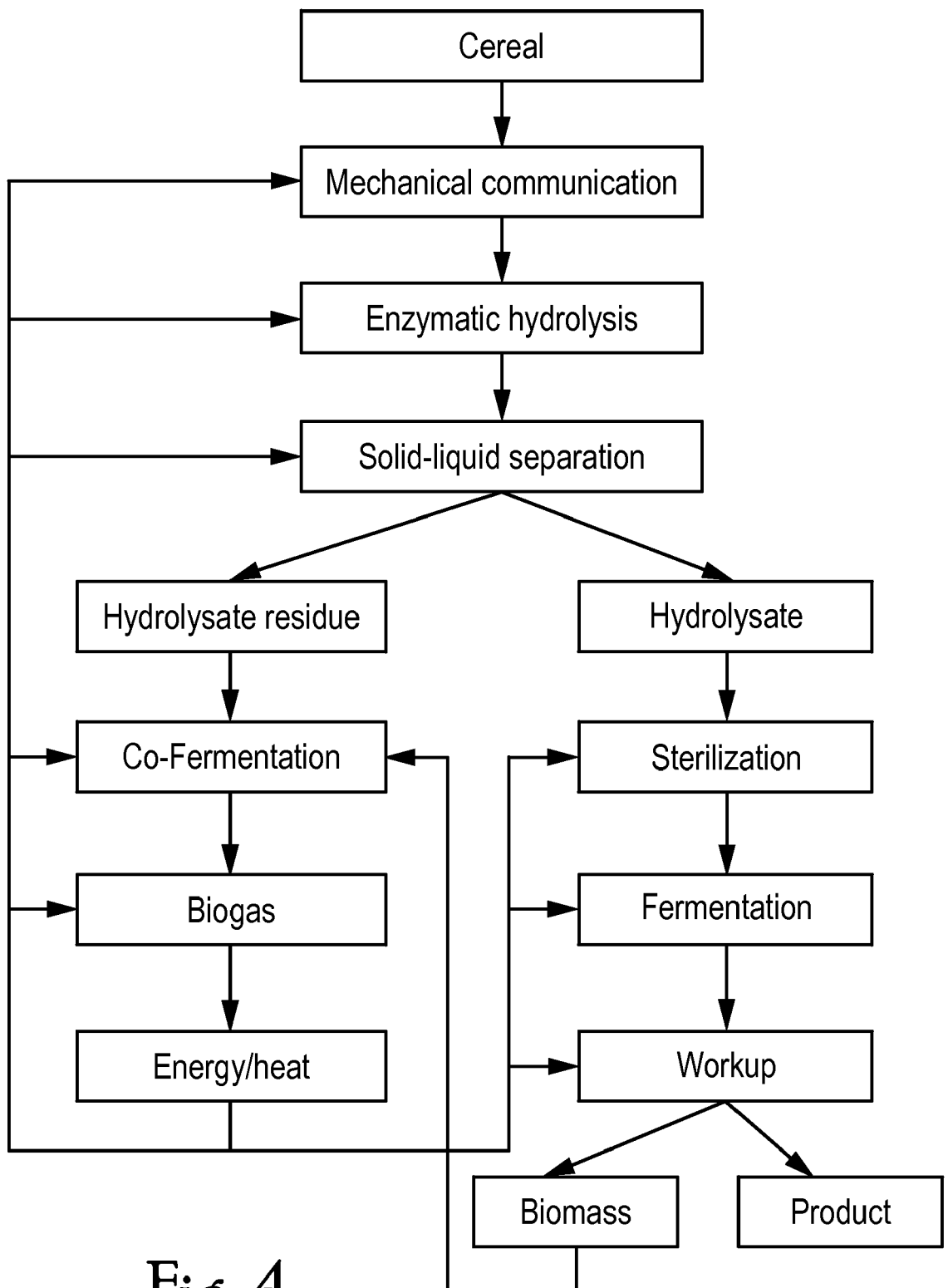
FIG. 4 is a flow-chart depicting an embodiment of the invention demonstrating how biomass waste produced from the fermentation of the hydrolysate may be fed into the anaerobic fermentation step to produce additional biogas through co-fermentation and how energy and/or heat produced from the combustion of biogas may be introduced at one or more steps of the overall process.

The most complete energetic exploitation and most complete integration is provided by the process sequence according to FIG. 4.

There, the energy and heat obtained in the fermentation process is fed into the integrated process at one or more points, while energy is simultaneously obtained from the biomass in the fermentation stage.

The inventive integrated process is found to be inexpensive since renewable raw materials are used. The fibrous wastes which are obtained in the workup of the renewable raw materials to give carbon sources utilizable in the fermentation by enzymatic hydrolysis are removed before the fermentation and fermented to give biogas which is generally converted further to electrical energy or heat. Specifically, at least some process steps are supplied with the energy or heat obtained and the net energy requirement of the integrated process is thus reduced. In a particular embodiment, the biomass obtained in the fermentative preparation is fed transversely into the biogas production as a coreactant and thus increases the biogas yield. The coreactant for the biogas preparation (biomass from the target substance preparation) is of comparatively constant quality, which in turn favours a reproducible process regime in the biogas production. Overall, significantly smaller amounts of waste products and by-products are obtained than in known part-processes.

LITERATURE

Blaesen M, Flaschel E, Friehs K (2006) Chem. Ing. Tech 78(3): 267-272
Busch R, Hirth T, Liese A et al. (2006) Chem. Ing. Tech. 78(3): 219-228
Eder B, Schulz H (2006) Biogas—Praxis: Grundlagen, Planung, Anlagenbau, Beispiele, Wirtschaftlichkeit, 3rd ed., Ökobuch Verlag, Staufen
Georgi T, Rittmann D, Wendisch V F (2005) Metab, Eng. 7(4): 291-301
Ikeda M (2003) Adv. Biochem. Eng. Biotechnol. 79:1-35
Pfefferle W, Möckel B, Bathe B, Marx A (2003) Adv. Biochem. Eng. Biotechnol. 79:59-112
Lyons T P (2003) pp. 1-7 in: Jacques K A et al. (eds.) The alcohol textbook, 4th ed. Nottingham University Press, Nottingham
Mulder R (2003) Biological wastewater treatment for industrial effluents: technology and operation, Paques B. V., Balk
Viesturs U, Dubrovskis V, Sakse A, Ruklisha M (1987) Proc, Latv. Acad. Sci. 8(481):

Experimental Description

1.

TABLE 1

| Enzymes used | |
|---|---|
| Spirizyme ® Plus (amyloglucosidase) | Novozymes, Denmark |
| Termamyl ® SC (alpha-amylase) | Novozymes, Denmark |
| Shearzyme ® 500 L (xylanase) | Novozymes, Denmark |
| BAN (alpha-amylase) | Novozymes, Denmark |

2. Enzymatic Hydrolysis 2.1. Flours of maize (whole-maize flour), of wheat (fine whole-wheat meal) and of rye (whole-rye flour and fine whole-rye meal) were hydrolysed enzymatically. To this end, 300 g of flour were suspended in 610 ml of water (33% w/w). The stirrer vessel used was a Braun B-DCU bioreactor with a pH electrode, temperature control, waste air cooler, disc stirrer and baffles.

For the phases of suspension, liquefaction and saccharification, the enzymes listed in Table 1 were added and the appropriate parameters were set (see Table 2). To adjust the pH, 2.5M sulphuric acid was used. The supernatant was tested for glucose content with the 7100MBS instrument from YSI. The reaction was ended approx. 28 hours after the start of the liquefaction step.

TABLE 2

| Parameters of the hydrolysis | | | |
|---|---|---|---|
| | Suspension | Liquefaction | Saccharification |
| Addition of enzyme | 0.051 ml Shearzyme[1], 0.3 ml BAN[2] | 0.12 ml Termamyl SC | 0.270 ml Spirizyme Plus |
| pH | 5.7 | 5.5-5.8 | 4.5-5.0 |
| T [min] | 30 | 90 | approx. 28 |
| T [° C.] | 55 | 85 | 60 |
| Stirrer speed [rpm] | 800 1500 (rye) | 1000 | 1000 |

[1]only for wheat and rye flours
[2]only for rye flours 2.2 Washing

The washing of the glucose out of the solid residue was performed batchwise.

For each batch, the mixture was resuspended in demineralized water and centrifuged. The washing operation was ended when less than 1% of the starting concentration of glucose was detectable in the washing water.

2.3 Concentration

The hydrolysates of fine whole-wheat meal, whole-rye flour and fine whole-rye meal were concentrated in a vacuum evaporator. The tests were performed at different temperatures and applied pressures. The mass concentration of glucose in the solutions was determined before and after the concentration step.

2.4 Sterilization

The sterilization tests were performed with the concentrated fine whole-wheat meal/glucose solutions. For each test, 7 g of solution were weighed into a 100 ml glass bottle. In an autoclave of capacity 75 l, the appropriate hold times and sterilization temperatures were established. During the operation, the temperature and pressure data in the autoclave were recorded by a data logger. These data were intended to serve as a comparison of the different experiments.

A spectrophotometer was used to record the absorbance of the solutions in the range of wavelengths of 200 nm to 800 nm.

3. Mass Balance

The mass balance is intended to determine the yield of glucose per amount of raw material used. The recovery value is to be found and the integrity of the balance is to be shown. This includes the quantification of the solid residue and of the proportion of proteins, lipids, pentosans, glucose and other sugars in the solution.

As the basis for the mass balance, the residual moisture content, the pentosan content and the starch content of the flours used was determined. The aqueous phase of the hydrolysate was analysed for its protein content. The aqueous supernatant of a whole-corn flour hydrolysis was analysed. The protein concentration was 0.66 mg/ml. This corresponded to 0.05% of the flour weight. It can thus be assumed that only negligible amounts of the protein go into solution, i.e. that the protein detected can be ascribed to the enzymes added. For comparison, the protein content in cornflour is 9.2%; the protein content is therefore suspected to be in the solid residue.

Figure 5:
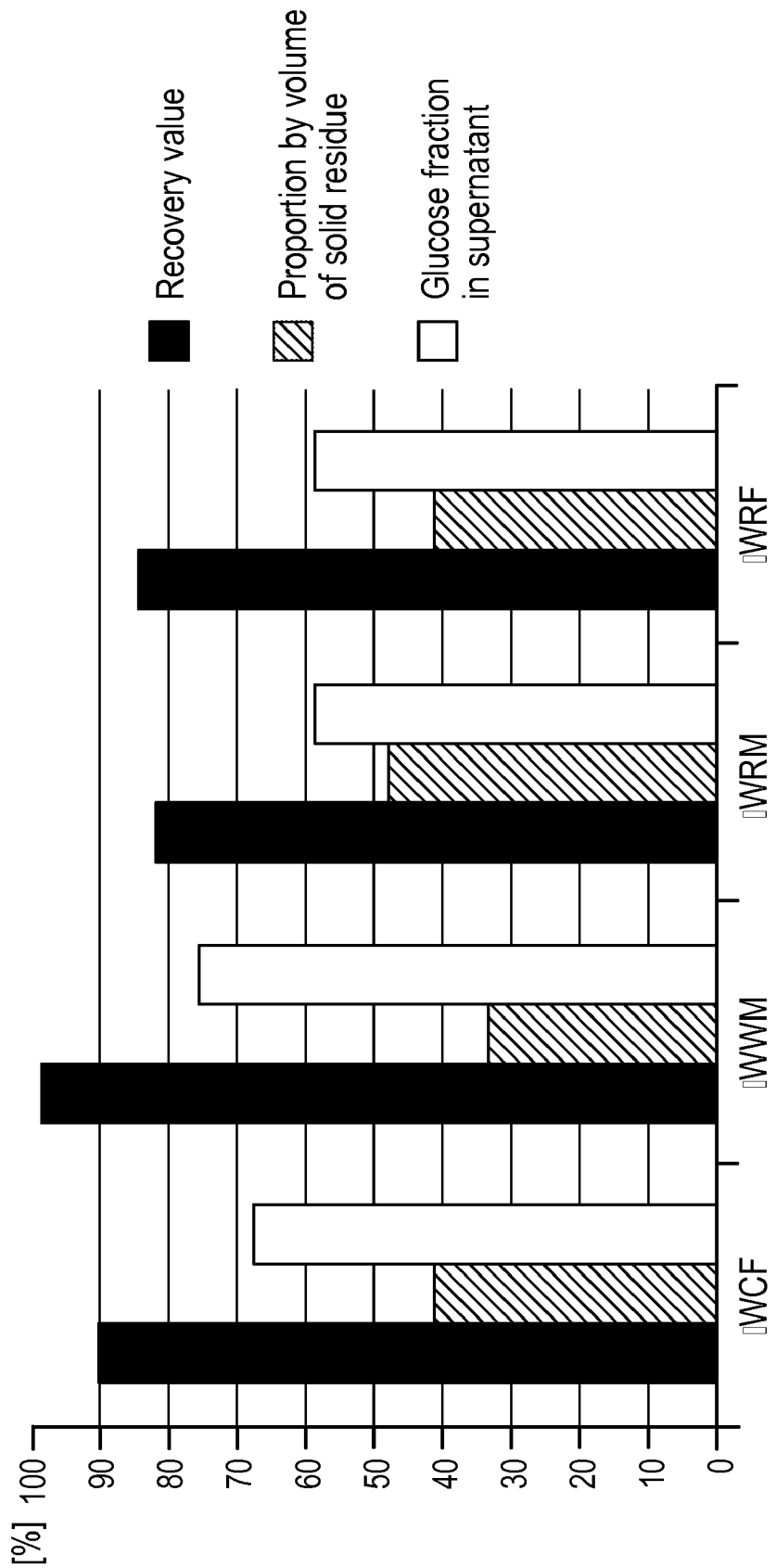
FIG. 5 depicts the recovery values, proportion by volume of solid residue, and glucose yields from the enzymatic hydrolysis of whole corn flour (WCF), whole wheat meal (WWM), whole rye meal (WRM), and whole rye flour (WRF).

The recovery values are shown in FIG. 5. The integrity of the mass balance had the best value of 98% for fine whole-wheat meal, WWM. The integrity was 90.2%, and 83.5% and 81% for whole-rye flour and fine whole-rye meal, WRF and WRM, respectively. The figure also shows the relation of the proportion by volume of solid residue. The solid residue of fine whole-wheat meal was comparatively the smallest. This also means that the glucose content in the supernatant was the highest. The ratio of glucose in the supernatant and solids content is similar for the whole-corn flour, whole-rye flour and fine whole-rye meal hydrolysates. The greater the solids volume, the less glucose is found in the supernatant. This means that the glucose solution is included in the solid.

4. Experiments on Solid Removal

Centrifugation experiments were performed with the hydrolysis suspensions of fine whole-wheat meal, whole-rye flour, fine whole-rye meal and whole-corn flour. Samples were centrifuged in graduated vessels at 4800 RCF for 20 min (Minifuge; Heraeus). In further experiments, the behaviour in the solids removal in the fine whole-wheat meal hydrolysate was investigated (Table 3).

4.1 Properties of the Suspension

TABLE 3

|  | Method | Instrument |
| --- | --- | --- |
| Viscosity | Rotary viscometer | Haake; Rheostress 600 |
| Conductivity | Conductometric | WTW; LF 323 |
| Zeta potential | Determination of isoelectric point | DT 1200 |
| Particle size distribution | Laser diffraction spectrometer | HORIBA LA920 |
| pH | pH electrode | Mettler-Toledo |
| Chemical composition of the fines | Elemental analysis |  |
| Buffer action of the hydrolysate | Titration with 1M hydrochloric acid | pH electrode; Mettler-Toledo |

4.2 Filtration

Filtration of the suspension was performed in a filter cell to which pressure can be applied. The filter area was 20 cm². The flux was recorded by means of a balance with a coupled detection system (Filtratest®; BOKELA). After the end of the filtration, cake thickness and dry substance content of the cake were determined.

4.3 Filter Centrifuge

Filtration was performed in a centrifugal field (Megafuge 1.0; Heraeus) in a filter cup at a spin index of 1500 g and times between one minute and ten minutes. In addition, temperature and pH were varied (see results and discussion). The filter area was 15 cm². After the end of the operation, cake thickness and dry substance content of the cake were determined.

4.4 Sedimentation

The sedimentation was carried out in a centrifugal field in graduated 10 ml centrifuge bottles. The spin index was in each case 3000 g. pH, temperature and centrifugation time were varied. The proportion by volume of supernatant and solid phases was determined, and also the dry substance content of the solid phases.

4.5 Biogas Formation from Hydrolysate Residue

Figure 6:
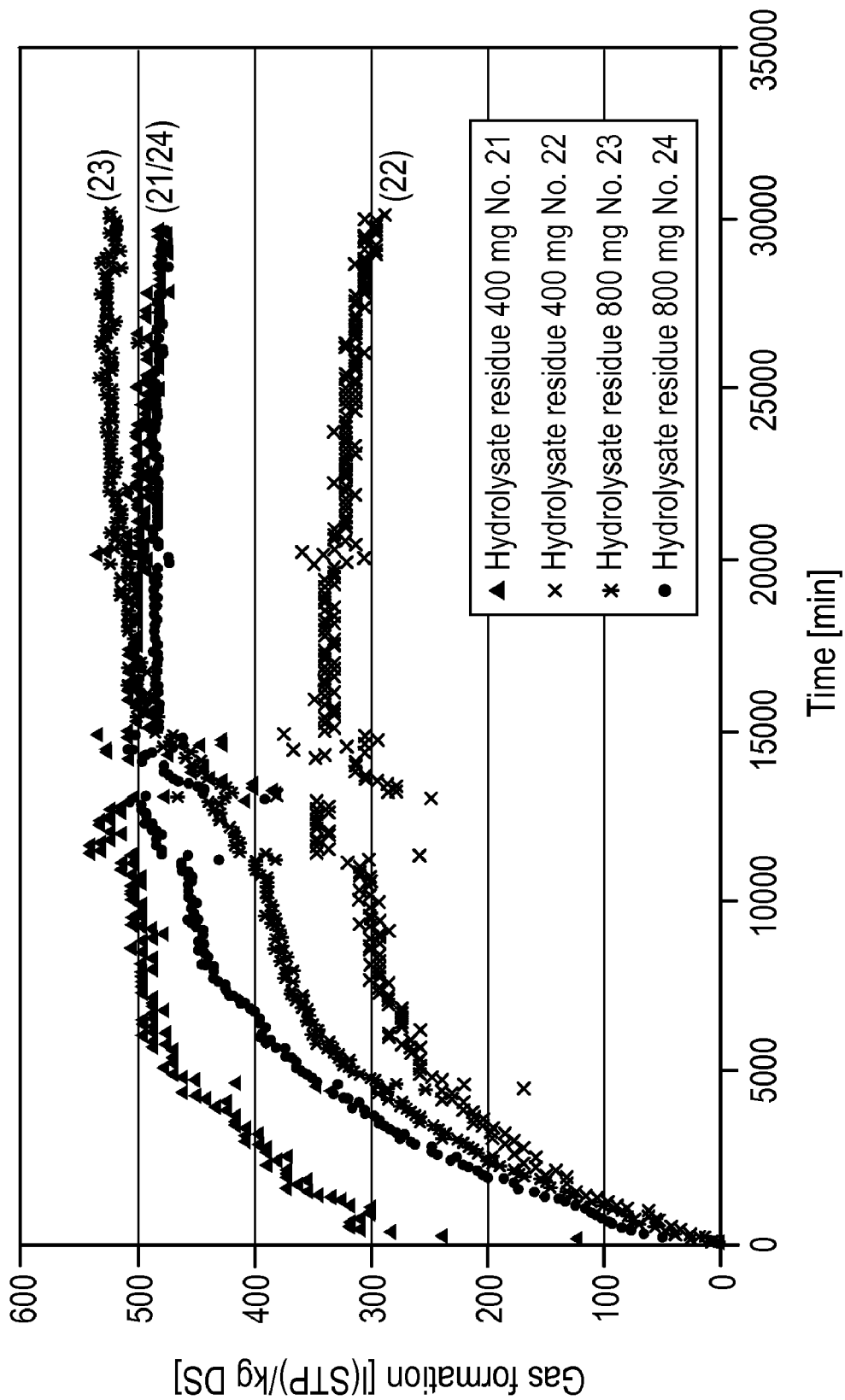
FIG. 6 depicts biogas production formed from anaerobic degradation of hydrolysate residues.
Figure 7:
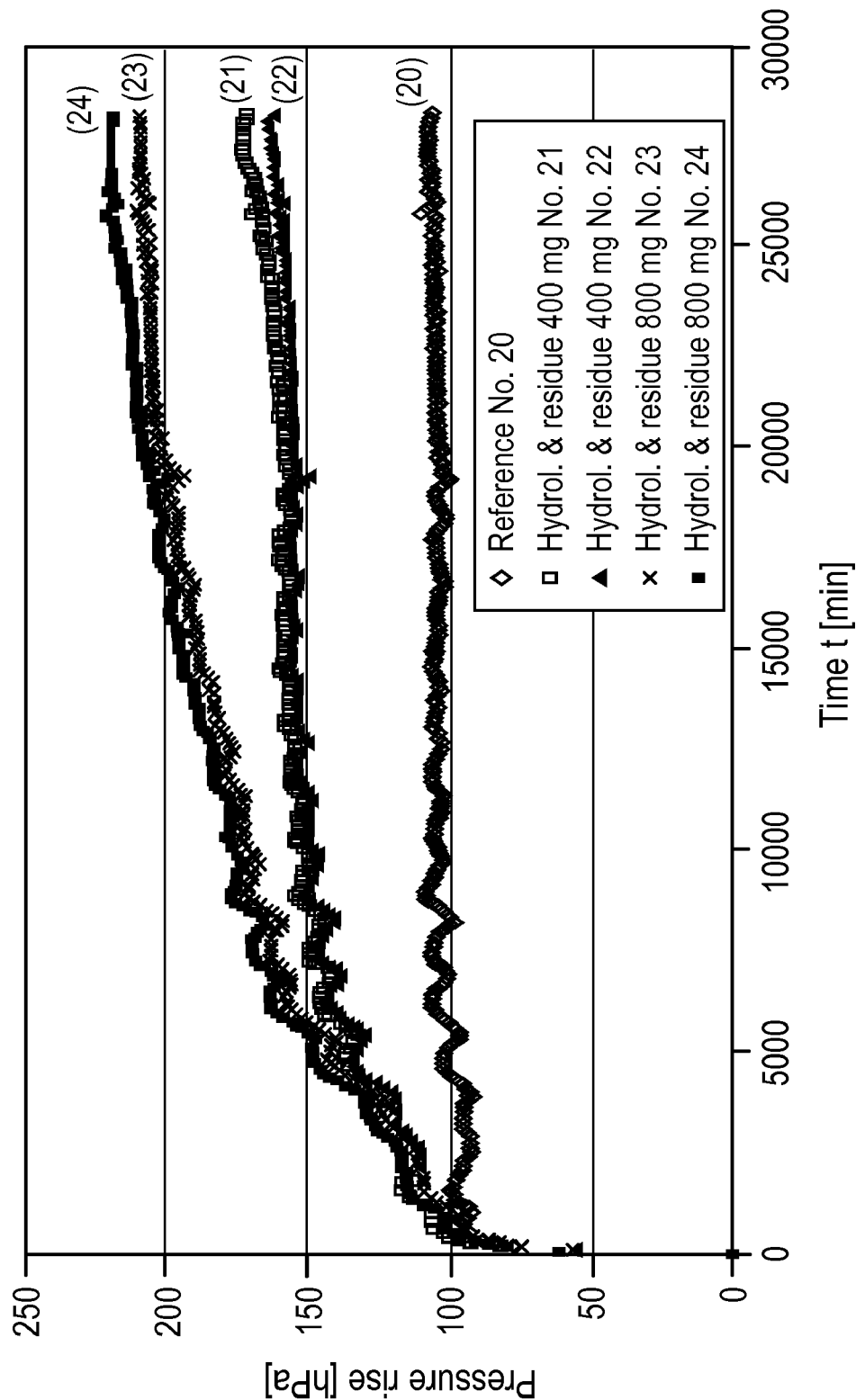
FIG. 7 depicts biogas production formed from anaerobic degradation of hydrolysate and fermentation residues.

The amount of biogas and its methanol content were determined by the OxiTop®-Control test system on the laboratory scale. The measurement is based on the pressure rise as a result of the formation of biogas in the measuring bottle (FIG. 6).

First, the volume of the gas space of the measuring bottles used was determined including all internals (rubber stopper, magnetic stirrer bar). The thermostat cabinet was adjusted to 35° C. and a stirrer board is installed. The tap water intended for use and the fresh digestion sludge were degassed with nitrogen for a few minutes in order to eliminate oxygen present, and heated to 35° C. Before the start of the experiment, the digestion sludge was exhausted for between one and five days.

The measurement bottles were placed on an inductive stirrer system with a magnetic stirrer bar and filled with 400 ml of the prepared tap water. Thereafter, the weighed hydrolysate residue, which consists especially of fibre fractions, was added and a substantially anaerobic atmosphere was ensured by sparging the bottles with nitrogen. The vessel containing digestion sludge was likewise sparged with nitrogen. After stirring, 50 ml thereof were transferred to the measurement bottle with a pipette. After the pH was measured, it was corrected if appropriate to pH 7±0.2 with dilute hydrochloric acid or sodium hydroxide solution (0.5 mol/l). The bottles were sealed and, after activation of the measurement heads, incubated at 35° C. in the dark with stirring (approx. 130 rpm). To take account of the gas formed by the digestion sludge itself, an experiment without hydrolysate residue was also started (experiment 19 in Table 4).

The basis of the evaluation is formed by the ideal gas law:

$$p \cdot V = n \cdot R \cdot T$$

With the pressure p [Pa], the temperature T [K], the universal gas constant R [J/(mol·K)] and the gas volume V [m³] of the bottle, it is thus possible to calculate the amount n [mol] of gas formed.

The results of the amounts of gas formed are as summarized in Table 4:

TABLE 4

Amount of gas formed

| | Bottle No. | | | | |
|---|---|---|---|---|---|
| | 19 | 21 | 22 | 23 | 24 |
| Sample | Reference | 0.4 g hydrol. | 0.4 g hydrol. | 0.8 g hydrol. | 0.8 g hydrol. |
| Gas volume of the bottles [ml] | 705 | 707 | 708 | 707 | 706 |
| Amount of gas at start of experiment [mol] | 0.0292 | 0.0293 | 0.0293 | 0.0292 | 0.0292 |
| Total amount of gas [mol] | 0.0360 | 0.0375 | 0.0372 | 0.0393 | 0.0394 |
| Amount of newly formed gas [mol] | 0.0068 | 0.0083 | 0.0079 | 0.0101 | 0.0102 |
| Amount of gas from hydrolysate residue [mol] | — | 0.0015 | 0.0010 | 0.0033 | 0.0034 |
| $CH_4$ content in amount of hydrol. gas [%] | — | 41 | 68 | 62 | 58 |
| $CO_2$ content in amount of hydrol. gas [%] | — | 4 | 15 | 31 | 27 |
| Sum of $CO_2$ and $CH_4$ [%] | — | 45 | 84 | 93 | 84 |

The content of methane and carbon dioxide in the amount of gas formed from the hydrolysate residue was between 84% and 93% for experiments No. 22, No. 23 and No. 24.

4.6 Biogas Formation from Cofermentation of Hydrolysate Residue and Biomass from the (Target Product) Fermentation The experiments were performed analogously to 4.5. The total amount of dry substance obtained is formed from the fermentation residue to an extent of 39% and from the hydrolysate residue to an extent of 61%.

Table 5 shows the methane and carbon dioxide contents measured in percent by volume, and also the absolute amounts minus gas formed by the reference sample itself. The hydrogen sulphide content was not determined since the value was below the gas chromatography threshold of 0.05% by volume both for the fermentation of the hydrolysate residue and for that of the fermentation residue.

TABLE 5

Amounts of methane and carbon dioxide in the cofermentation

| | Bottle No. | | |
|---|---|---|---|
| | 20 | 21 | 24 |
| Sample | Reference | 0.4 g hydrol. & residue | 0.8 g hydrol. & residue |
| Absolute pressure at end of experiment [hPa] | 1129 | 1194 | 1241 |
| Amount of gas [mol] | 0.0311 | 0.0330 | 0.0342 |
| $CH_4$ content [% by vol.] | 1 | 3.7 | 6 |
| $CO_2$ content [% by vol.] | 0.9 | 1.8 | 2.5 |
| $CH_4$ content [mol] | 0.00031 | 0.00122 | 0.00205 |
| $CO_2$ content [mol] | 0.00028 | 0.00059 | 0.00086 |
| Amount of $CH_4$ minus reference [mol] | — | 0.00091 | 0.00174 |
| Amount of $CO_2$ minus reference [mol] | — | 0.00031 | 0.00058 |

4.7 Comparison of Mono- and Cofermentation

A comparison of the absolute amounts of methane of 355 l (STP)/kg oDS (standard litres/kg oDS (organic dry substance used)) in the case of proportional addition of the amounts of gas in the monofermentation experiments and 430 l (STP)/kg oDS in the cofermentation experiment shows that the cofermentation can achieve significantly higher mass-based amounts of methane. Cofermentation is thus preferable over monofermentation.

4.8 Degree of Degradation of the Hydrolysate

The degree of degradation indicates how many percent of the organic dry substance is degraded within the given residence time.

For this calculation, the molar amounts of methane and carbon dioxide determined were converted to weight and based on the amount of substrate used.

Table 6 shows the calculated degree of degradation of the hydrolysate residue.

TABLE 6

Degree of degradation of the hydrolysate residue

| | Bottle No. | |
|---|---|---|
| | 23 | 24 |
| Sample | 0.8 g hydrolysate | 0.8 g hydrolysate |
| Amount of $CH_4$ [mol] | 0.00205 | 0.00193 |
| Amount of $CO_2$ [mol] | 0.00101 | 0.00089 |
| Weight of $CH_4$ [g] | 0.0328 | 0.0310 |
| Weight of $CO_2$ [g] | 0.0443 | 0.0394 |
| Total weight of the gas [g] | 0.0771 | 0.0704 |
| Amount of oDS hydrolysate residue [g] | 0.139 | 0.139 |
| Degree of degradation [%] | 56 | 51 |

It shows good agreement for the two samples and is an average of 54%. This reduces the amount of hydrolysate residue (organic dry substance) to be disposed of by 54% as a result of coupling of the biogas production to the hydrolysis step.

4.9 Coupling of Hydrolysis, Fermentation and Biogas Production

The example is based on a hydrolysis plant with a capacity of 100 000 t/a glucose equivalent. The plant is coupled to a fermentation plant for preparing L-lysine. The glucose solution produced is concentrated to the concentration needed for the fermentation and sterilized. These operations are very energy-intensive. The energy demand of such a plant is approx. 625 GWh/a. The biogas production (cofermentation) produces approx. 47.6 GWh/a of electricity and approx. 52.3 GWh/a of heat. For the present example, approx. ⅙ of the total energy requirement of the hydrolysis, which is coupled to the fermentation to prepare the target product, is covered by the biogas production in accordance with the invention.

What is claimed is:

1. A process for integrated utilization of the products of an enzymatic hydrolysis of renewable raw materials used in preparing a proteinogenic amino acid, comprising:
   a) preparing an aqueous hydrolysis mixture of the renewable raw materials, wherein the aqueous mixture comprises at least one carbon source utilizable by a microorganism used in preparing the proteinogenic amino acid;
   b) subjecting the aqueous mixture to enzymatic hydrolysis, producing a hydrolysate and a hydrolysate residue thereby;
   c) separating the hydrolysate and the hydrolysate residue;
   d) subjecting the hydrolysate to aerobic fermentation by a microorganism, producing the proteinogenic amino acid and a biomass thereby; and
   e) subjecting the hydrolysate residue to anaerobic fermentation by a microorganism, producing a biogas thereby.

2. The process of claim 1, wherein the biomass is separated from the proteinogenic amino acid and anaerobically fermented, producing a biogas thereby.

3. The process of either claim 1 or 2, wherein the biogas is converted to energy.

4. The process of claim 3, wherein the energy is used in at least one step of the process.

5. The process of claim 1, in which the at least one carbon source comprises cereal grams.

6. The process of claim 5, in which the cereal grains are selected from the group consisting of maize, rye, wheat and barley.

7. The process of claim 1, wherein the microorganism is selected from one or more of the group consisting of the genera *Corynebacterium, Bacillus, Ashbya, Escherichia, Aspergillus, Alcaligenes, Actinobacillus, Anaerobiospirillum, Lactobacillus, Propionibacterium* and *Clostridium*.

8. The process of claim 7, wherein the microorganism is selected from one or more of the group consisting of *Corynebacterium glutamicum, Bacillus subtilis, Ashbya gossypii, Escherichia coli, Aspergillus niger* or *Alcaligenes latus, Anaerobiospirillum succiniproducens, Actinobacillus succinogenes, Lactobacillus delbrueckii, Lactobacillus leichmanni, Propionibacterium arabinosum, Propionibacterium schermanii, Propionibacterium freudenreichii, Clostridium propionicum* and *Clostridium acetobutlicum*.

9. A process for integrated utilization of the products of an enzymatic hydrolysis of renewable raw materials used in preparing a proteinogenic amino add, comprising:
   a) preparing an aqueous hydrolysis mixture of the renewable raw materials, wherein the aqueous mixture comprises at least one carbon source utilizable by a microorganism used in preparing the proteinogenic amino acid;
   b) subjecting the aqueous mixture to enzymatic hydrolysis, producing a hydrolysate and a hydrolysate residue thereby;
   c) separating the hydrolysate and the hydrolysate residue;
   d) subjecting the hydrolysate to aerobic fermentation by a microorganism, producing the proteinogenic amino acid and a biomass thereby;
   e) separating the proteinogenic amino acid from the biomass;
   f) subjecting the biomass and the hydrolysate residue to anaerobic co-fermentation by a microorganism, producing a biogas thereby.

10. The process of claim 9, in which the at least one carbon source comprises cereal grams.

11. The process of claim 9, wherein the microorganism is selected from one or more of the group consisting of the genera *Corynebacterium, Bacillus, Ashbya, Escherichia, Aspergillus, Alcaligenes, Actinobacillus, Anaerobiospirillum, Lactobacillus, Propionibacterium* and *Clostridium*.

12. A process for integrated utilization of the products of an enzymatic hydrolysis of renewable raw materials used in preparing a proteinogenic amino add, comprising:
   a) preparing an aqueous hydrolysis mixture of the renewable raw materials, wherein the aqueous mixture comprises at least one carbon source utilizable by a microorganism used in preparing the proteinogenic amino acid;
   b) subjecting the aqueous mixture to enzymatic hydrolysis, producing a hydrolysate and a hydrolysate residue thereby;
   c) separating the hydrolysate and the hydrolysate residue;
   d) subjecting the hydrolysate to aerobic fermentation by a microorganism, producing the proteinogenic amino acid and a biomass thereby;
   e) separating the proteinogenic amino acid from the biomass;
   f) subjecting the biomass and the hydrolysate residue to anaerobic co-fermentation by a microorganism, producing a biogas thereby;
   g) collecting and combusting the biogas, producing energy thereby; and
   h) supplying the energy to one or more steps of the process.

13. The process of claim 9, in which the at least one carbon source comprises cereal grams.

14. The process of claim 9, wherein the microorganism is selected from one or more of the group consisting of the genera *Corynebacterium, Bacillus, Ashbya, Escherichia, Aspergillus, Alcaligenes, Actinobacillus, Anaerobiospirillum, Lactobacillus, Propionibacterium* and *Clostridium*.

* * * * *